US 8,586,592 B2

(12) United States Patent
Xu

(10) Patent No.: US 8,586,592 B2
(45) Date of Patent: Nov. 19, 2013

(54) PHARMACEUTICAL FORMULATIONS COMPRISING VORICONAZOLE AND PROCESSES FOR PREPARATION THEREOF

(75) Inventor: Yongxiang Xu, Jiangsu (CN)

(73) Assignees: Nanjing Cavendish Bio-Engineering Technology Co., Ltd., Nanjing, Jiang (CN); Yongxiang Yu, Nanjing, Jiangsu (CN)

( * ) Notice: Subject to any disclaimer, the term of this patent is extended or adjusted under 35 U.S.C. 154(b) by 86 days.

(21) Appl. No.: 13/140,900

(22) PCT Filed: Dec. 31, 2009

(86) PCT No.: PCT/CN2009/076328
§ 371 (c)(1),
(2), (4) Date: Jun. 20, 2011

(87) PCT Pub. No.: WO2010/075801
PCT Pub. Date: Jul. 8, 2010

(65) Prior Publication Data
US 2011/0257197 A1    Oct. 20, 2011

(30) Foreign Application Priority Data

Dec. 31, 2008  (CN) .......................... 2008 1 0192985

(51) Int. Cl.
*A61K 31/506* (2006.01)
*A61P 31/00* (2006.01)

(52) U.S. Cl.
USPC ...................................................... 514/256

(58) Field of Classification Search
None
See application file for complete search history.

(56) References Cited

U.S. PATENT DOCUMENTS

| 6,616,941 B1 * | 9/2003 | Seo et al. .......................... 424/450 |
| 6,632,803 B1 * | 10/2003 | Harding ........................... 514/58 |
| 7,550,157 B2 | 6/2009 | Seo et al. |

FOREIGN PATENT DOCUMENTS

| CN | 1813751 A | 8/2006 |
| CN | 1861044 A | 11/2006 |
| CN | 101444510 A | 6/2009 |
| JP | 2003532688 A | 11/2003 |
| WO | WO98/58677 | * 12/1998 ............. A61K 47/40 |

OTHER PUBLICATIONS

Dong-ying et al. in Journal of China Pharmaceutical University 2008, 39(3):223-227.*
von Mach et al. in BMC Clinical Pharmacology 2006, 6:6, pp. 1-6.*
Synthesis of PLA-mPEG and Preparation of Docetaxel Polymer Micelles by Dong-ying Ji et al., Journal of China Pharmaceutical University 2008,39(3)223-227 dated Dec. 18, 2007.
International Search Report for PCT/CN2009/076328 dated Apr. 1, 2010.
Chi, Sang-Cheol, et al., "A Polymeric Micellar Carrier for the Solubilization of Biphenyl Dimethyl Dicarboxylate", Arch. Pharm. Res., vol. 26, No. 2, pp. 173-181, (2003).
Peng, Hai-sheng, et al., "Voriconazole into PLGA nanoparticles: improving agglomeration and antifungal efficacy", International Journal of Pharmaceutics, vol. 352, pp. 29-35, (2008).
Zhang, Xichen, et al., "An investigation of the antitumour activity and biodistribution of polymeric micellar paclitaxel", Cancer Chemother Pharmacol, vol. 40, pp. 81-86, (1997).

* cited by examiner

*Primary Examiner* — Dennis Heyer
(74) *Attorney, Agent, or Firm* — MacMillan, Sobanski & Todd, LLC

(57) ABSTRACT

The present invention provides a pharmaceutical formulation comprising voriconazole or a pharmaceutically acceptable derivative thereof, and an excipient of formula (I), i.e., monomethoxy poly(ethylene glycol)-poly (D,L-lactic acid) block copolymers (mPEG-PDLLA). The pharmaceutical formulation of the present invention has been shown to be stable and safe by experiments.

1 Claim, 6 Drawing Sheets

PHARMACEUTICAL FORMULATIONS COMPRISING VORICONAZOLE AND PROCESSES FOR PREPARATION THEREOF

CROSS-REFERENCE TO RELATED APPLICATIONS

This application is the National Phase of International Application PCT/CN2009/076328 filed 31 Dec. 2009, which designated the U.S. That International Application was published in English under PCT Article 21(2) on Aug. 28, 2010 as International Publication Number WO 2010/075801A1. PCT/CN2009/076328 claims priority to Chinese Application No. 200810192985.7 filed 31 Dec. 2008. Thus, the subject nonprovisional application also claims priority to Chinese Application No. 200810192985.7 filed 31 Dec. 2008. The disclosures of both applications are incorporated herein by reference.

TECHNICAL FIELD

The present invention relates to the pharmaceutical formulation technology, specifically, to a pharmaceutical formulation comprising voriconazole and monomethoxy poly(ethylene glycol)-poly(D,L-lactic acid) block copolymers (mPEG-PDLLA), and its preparing process.

BACKGROUND ART

The chemical structure of voriconazole (CAS No.:137234-62-9) had been disclosed in European patent EP 0440372A1, as following:

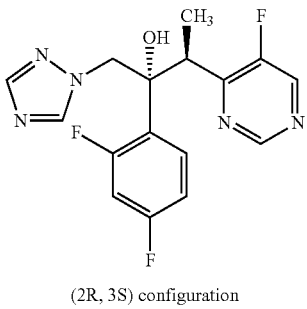 [SMILES: C[C@@H](c1ncncc1F)[C@](O)(Cn1cncn1)c1ccc(F)cc1F]

(2R, 3S) configuration

The product was approved by the US FDA in May, 2002, its brand name as Vfend or WEIFAN (in PINYIN). Voriconazole is a second-generation synthetic triazole antifungal agent, its mechanism of action is to inhibit the demethylation of 14 α-lanosterol mediated by cytochrome P-450 in fungi, thereby to inhibit the biosynthesis of ergosterol. The studies in vitro has shown that voriconazole has a broad spectrum of antifungal action. The drug has been shown to be active against Candida species (including strains of *Candida krusei, Candida glabrata*, and *Candida albicans* resistant to fluconazole), and has been shown to be active against all tested Aspergillus fungi. Furthermore, voriconazole exhibits in vitro activity against other pathogenic fungi, including those with reduced susceptibility to current available antifungal agents, such as *Scedosporium* and *Fusarium* species. In conclusion, voriconazole has a broad spectrum and more potency of antifungal virtue, particularly good efficacy in the treatment of infiltrating infection by invasive *Aspergillus*. The approved dosage forms of voriconazole include: lyophilized powder for injection, tablets, dry suspension, which could be orally or i.v. administrated, wherein intravenous administration is mainly applied in ICU (intensive care unit) during or after the operation of oncology, hematology, department of burns, and general surgery. Because solubility of voriconazole in water is very little (almost insoluble at pH=7, and 0.2mg/ml at pH=3), it is unstable in water, and susceptible to be hydrolysized into its enantiomeric configuration (2S,3R). Therefore, an intravenous aqueous formulations with enough shelf life would be developed until the key issue of its solubility has been settled. These problems becomes more serious to semi-polar compound of voriconazole (logD=1.8), because there are no conventional way, such as adding oil and surfactants and the like, could dissolve voriconazole.

The European patent EP 0440372A1 taught to formulate voriconazole with cyclodextrin, however, so far it is generally suspected that the underived or unmetabolized cyclodextrin may cause toxic adverse effect to human body, and be unsuitable to be a pharmaceutical excipient.

In the lyophilized formulation of voriconazole for injection marketed by Pfizer Co., the solubility of voriconazole was increased by using a kind of solubilizer, sulfobutyl ether β-cyclodextrin sodium (SBECD). The amount of SBECD in 1 milligram of lyophilized formulation of approved voriconazole (labeled amount) is about 15 mg~18 mg (1:15), therefore a large amount of sulfobutyl ether β-cyclodextrin sodium was used in the lyophilized formulation, and encapsuled voriconazole to increase its solubility. This method substantially resolve the problem of water solubility of voriconazole. However, with the deeper investigations on β-cyclodextrin serial derivatives, it was worried about the safety of clinically application of sulfobutyl ether β-cyclodextrin sodium. More and more studies in pharmacology and toxicology had demonstrated that β-cyclodextrin derivatives including sulfobutyl ether β-cyclodextrin sodium would be highly risky to human body. The toxicological studies on repeated administration of sulfobutyl ether β-cyclodextrin sodium had shown that SBECD primarily effected the vacuale formation in the urinary-tract epithelium, as well as activated macrophages in liver and lung. The positive result had been obtained from guinea pig maximization test (GPMT), which indicated that the intravenous formulation had the possibility of causing the allergy. In the two-year animal teratogenicity and carcinogenecity experiments, there were evidences to demonstrate that it was carcinogenic (pancreatic carcinoma) in rodent, and the results of studies also indicated its possibility of carcinogenesis in human. The primary disadvantages of sulfobutyl ether β-cyclodextrin sodium existed in the renal toxicity and hemolysis. Metabolism of this excipient in vivo mainly depended on the renal metabolism. Particularly hydroxypropyl-β-cyclodextrin, an impurity incorporated by the excipient itself, which was more renal toxic, as well as voriconazole itself, therefor the combination of these two components in the lyophilized formulation for intravenous administration clinically restricted to those patients with renal insufficiency and should be strictly used with caution! The results in hemolytic studies of sulfobutyl ether β-cyclodextrin sodium had shown that mild hemolysis could occur at 0.02 mg/ml in the route of intravenous administration, and significant heamolysis at 0.04 mg/ml. The results in long-term toxicity studies of sulfobutyl ether β-cyclodextrin sodium demonstrated that the course of treatment shouldn't be beyond 6 months with lyophilized pharmaceutical formulation for intravenous administration comprising voriconazole and sulfobutyl ether β-cyclodextrin sodium. Because the excipient had the above disadvantage, European Pharmaceutical Affairs Committee, US FDA and Chinese SFDA have required to scientifically re-evaluate the safety of this kind of pharmaceutical excipients. Because The solubility of voriconazole increased by sulfobutyl ether β-cyclodextrin sodium may cause the issues of its safety when applied clinically, it is important that a more scientific and safe voriconazole formulation for injection should be developed.

Pharmaceutical Plant of Zhuhai Livzon Group in China had used a special organic solvent, which is an admixture of certain ratio (2:3) of propylene glycol and ethanol, to dissolve the sterile powder of voriconazole, subsequently dissolved in the transfusion to be infused, in order to resolve the problem of voriconazole's solubility. Although propylene glycol and ethanol are safe when clinically used at a lower dose, there are also obvious disadvantages when this solvent solubilization method is clinically applied: firstly, special organic solvent to dissolve voriconazole (because 100 mg of sterile powder requires to be dissolved in 5 ml (2:3) of propylene glycol and ethanol, and the dosage for an adult is generally 400 mg of voriconazole, which requires to be dissolved in 20 ml (2:3) of propylene glycol and ethanol) in blood stream is mainly metabolized by liver and kidney, as a result, the organic solvent in blood aggravates the metabolic load of patient's liver and kidney. Secondly, the special organic solvents greatly interfere the detection of bacterial endotoxin, as a result the detection and quality controlling become difficult. Thirdly, the improvement for the solubility of voriconazole by these special organic solvents is still quite limited, when 400 mg of voriconazole is generally administrated to an adult, which requires to use 20 ml of propylene glycol and ethanol to dissolve, and then 500 ml infusion at least is required to dilute for transfusion, if 250 ml of infusion is used to dilute, the crystal may be precipitated, resulting in high risk in the safety. Although 500 ml of infusion has been used for dilution, the stability of the resulting solution is still greatly effected by the temperature of environment. In conclusion, it is very inconvenient in clinical application, and difficult to be extended.

In addition, it has shown that there is a disadvantage in the stability of product, because the inactive enantiomer of voriconazole has been detected in the accelerated experiment of the above voriconazole injection marketed.

DISCLOSURE OF THE INVENTION

The present invention has overcome the above disadvantages by using an excipient—"monomethoxy poly(ethylene glycol)-poly(D,L-lactic acid) block copolymers (mPEG-PDLLA)"—to increase the solubility of voriconazole, especially solubility of voriconazole in water.

An objective of the present invention is to provide a novel pharmaceutical formulation comprising voriconazole and monomethoxy poly(ethylene glycol)-poly(D,L-lactic acid) block copolymers.

Another objective of the present invention is to provide a process for preparing the above-mentioned pharmaceutical formulation.

In one embodiment, the present invention provides a pharmaceutical formulation comprising voriconazole or a pharmaceutically acceptable derivative thereof including acid additional salt and acid ester, such as hydrochloride salt, phosphoric acid ester, etc., and a copolymer of formula (I) as following:

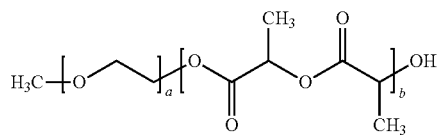

molecular formula: $CH_3(C_2H_4O)_a(C_6H_8O_4)_bOH$ wherein, a in the copolymer is 30~55, b is 10~55; preferably, a is 35~50, and b is 12~36; the most preferably, a is 40~45, and b is 14~30;

the average molecular weight is in the range of 2800~10000, preferably, 3300~7500, the most preferably, 3800~6300.

In the present invention, the said pharmaceutically acceptable derivative of voriconazole includes a pharmaceutically acceptable acid additional salt, for example, hydrochloride, hydrobromide, sulphate, phosphate, methanesulphonate, maleate, fumarate, benzenesulphonate or p-toluenesulphonate salts; or pharmaceutically acceptable acid ester, for example phosphoric acid ester (its preparing method refers to Chinese patent ZL 97192005.2), etc.

In a preferred embodiment, the invention provides a pharmaceutical formulation comprising voriconazole or a pharmaceutically acceptable derivative thereof, and copolymers of formula (I), wherein, the content of voriconazole or a pharmaceutically acceptable derivative thereof (based on voriconazole) is 2.0%~20.0% by weight, preferably, 3.0%~10.0% by weight, more preferably, 3.5%~7.0% by weight; the weight ratio of voriconazole or a pharmaceutically acceptable derivative thereof (based on voriconazole) to copolymers of formula (I) is 1:5~1:40, preferably, 1:10~1:30, more preferably, 1:15~1:25.

In a more preferred embodiment, the pharmaceutical formulation is the one administrated parenterally, such as injections administrated intravenously, or intramusclely, or subcutaneously, preferably, is lyophilized injection or injection solution, most preferably, it is lyophilized injection.

The invention provides a lyophilized injection comprising voriconazole or a pharmaceutically acceptable derivative thereof and a copolymer of formula (I), wherein, the content of voriconazole or a pharmaceutically acceptable derivative thereof (based on voriconazole) is 2.0%~20.0% by weight, preferably, 3.0%~10.0% by weight, more preferably, 4.0%~7.0% by weight; the weight ratio of voriconazole or a pharmaceutically acceptable derivative thereof (based on voriconazole) to copolymers of formula (I) is 1:5~1:50, preferably, 1:10~1:30, more preferably, 1:15~1:25.

The lyophilized injection of the invention could be stored for a long term, and could be dissolved in aqua pro injection, and then be compatibly used for infusion.

In another aspect of the invention, a process for preparing the above pharmaceutical formulation is provided by the invention, comprising the following steps:

Specifically, the monomethoxy poly(ethylene glycol)-poly(D,L-lactic acid) block copolymers could be prepared by the reaction of certain ratio of monomethoxy poly(ethylene glycol) (commercially available from "Acros") and lactide (commercially available from "Acros") in an inert environment, catalyzed by a trace of Stannous octoate, in the condition that the reaction temperature is above 120° C., to produce an amphiphilic block copolymer with a certain molecular content. (the relative chemical or physical data of monomethoxy poly(ethylene glycol)-poly(D,L-lactic acid) block copolymers are detailed in the Drawings.)

To the monomethoxy poly(ethylene glycol)-poly(D,L-lactic acid) block copolymers prepared as above are added water and a organic solvent (such as acetonitrile, acetone, methanol, and ethanol, etc) or mixture thereof, then stirred to dissolve; under the continuously stirring, voriconazole (or solution of voriconazole in an organic solvent) is added and stirred to dissolve; then an appropriate amount of activated charcoal is added to the resulting homogeneous solution, and thoroughly stirred for 30 mins; filtered through 0.45 μm filter film to remove the activated charcoal; after the filtrate is filtered through 0.22 μm filter film, a certain volume of solution is filled in a vial, and lyophilized to offer the lyophilized formulation.

The advantageous technical effects of the present invention are shown: solubility and stability of the complex of voriconazole and excipient "monomethoxy poly(ethylene glycol)-poly(D,L-lactic acid) block copolymers (mPEG-PDLLA)" in water could be increased by applying freeze-dried (lyophilized) technology. An excipient "monomethoxy poly(ethylene glycol)-poly(D,L-lactic acid) block copolymers (mPEG-PDLLA)" suitable for formulation of the invention could insure the final lyophilized products containing high level of water (such as 3.0%, 4.0%, 5.0%), but will not affect the stability of drug.

In addition, experiments show that the application of the above excipient in the formulation could control and reduce the voriconazole to produce the inactive enantiomer (2S,3R) and other impurities.

The chemical name of inactive enantiomer transformed by voriconazole is (2S,3R)-2-(2,4-difluorophenyl)-3-(5-fluoropyrimidin-4-yl)-1-(1H-1,2,4-triazol-1-yl)-2-butanol, and its chemical structure is as following:

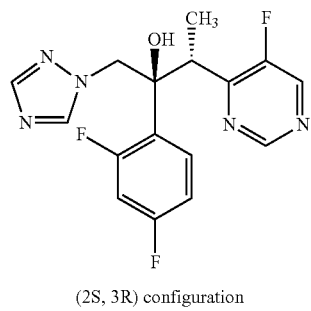 [SMILES: C[C@H](c1ncncc1F)[C@@](O)(Cn1cncn1)c1ccc(F)cc1F]

(2S, 3R) configuration

DESCRIPTION OF EMBODIMENTS

Figure 1:
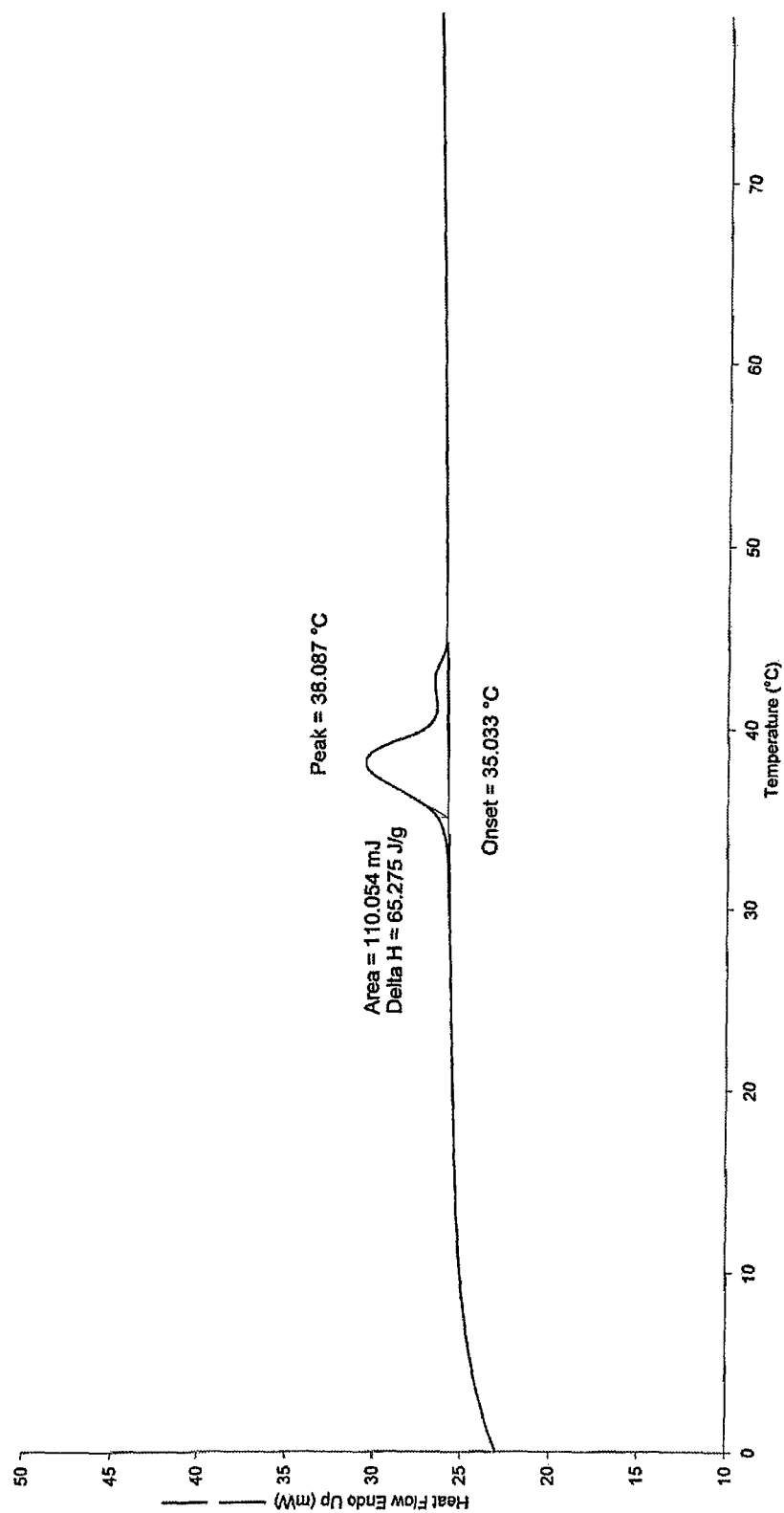
FIG. 1 is a DSC diagram of mPEG-PDLLA products prepared by solvent method of the invention (heat from 0° C. to 100° C., the rate of temperature rising is 10° C./min).
Figure 2:
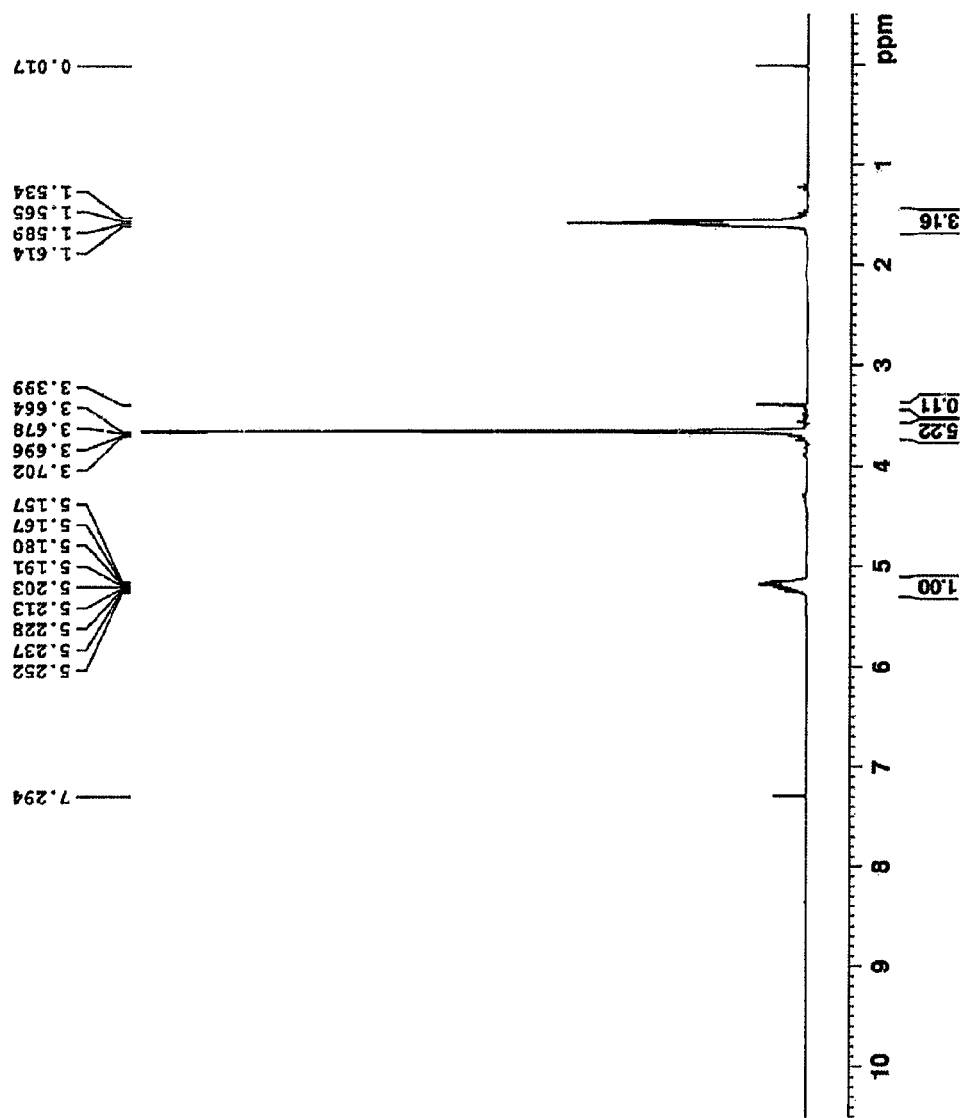
FIG. 2 shows a $^1$H-NMR spectrum of mPEG-PDLLA products prepared by solvent method of the invention ($^1$H-NMR CDCl$_3$ BRUKER DPX 300).
Figure 3:
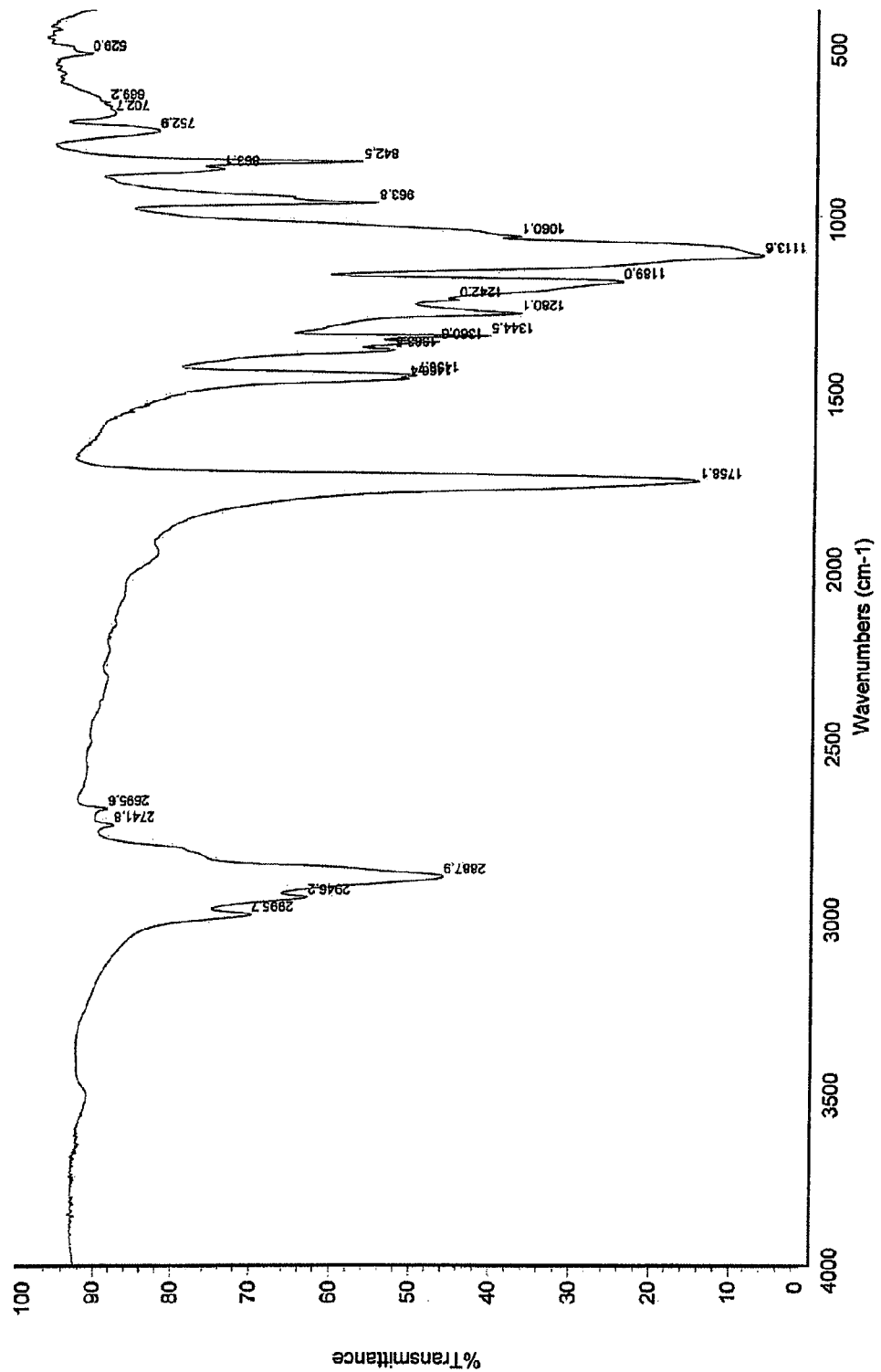
FIG. 3 shows a infrared absorption spectrum (Nexus 870 FT-IR) of mPEG-PDLLA products prepared by solvent method of the invention.
Figure 4:
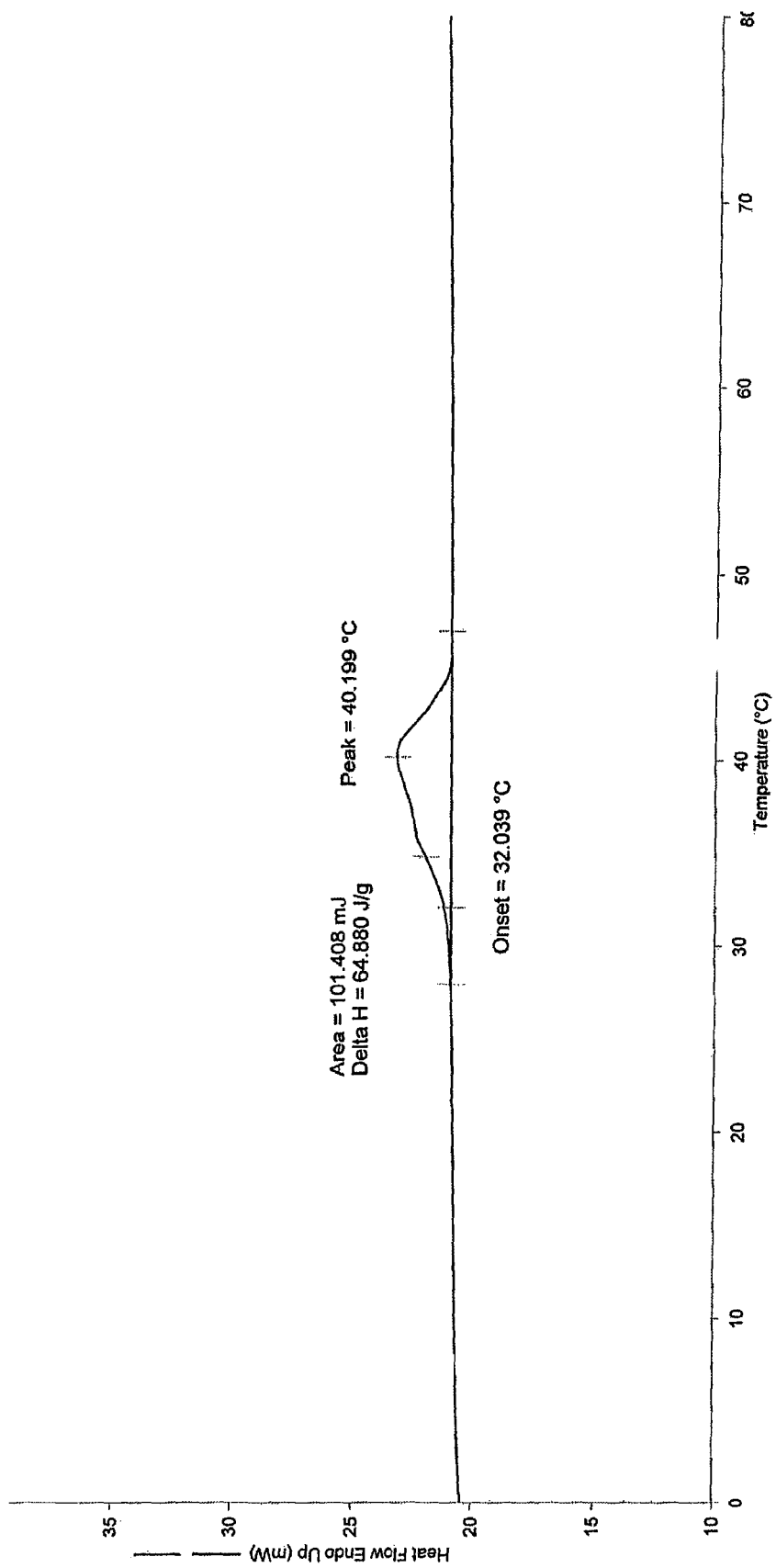
FIG. 4 is a DSC diagram of mPEG-PDLLA products prepared by vacuum method of the invention (heat from 0° C. to 100° C., the rate of temperature rising is 10° C./min).
Figure 5:
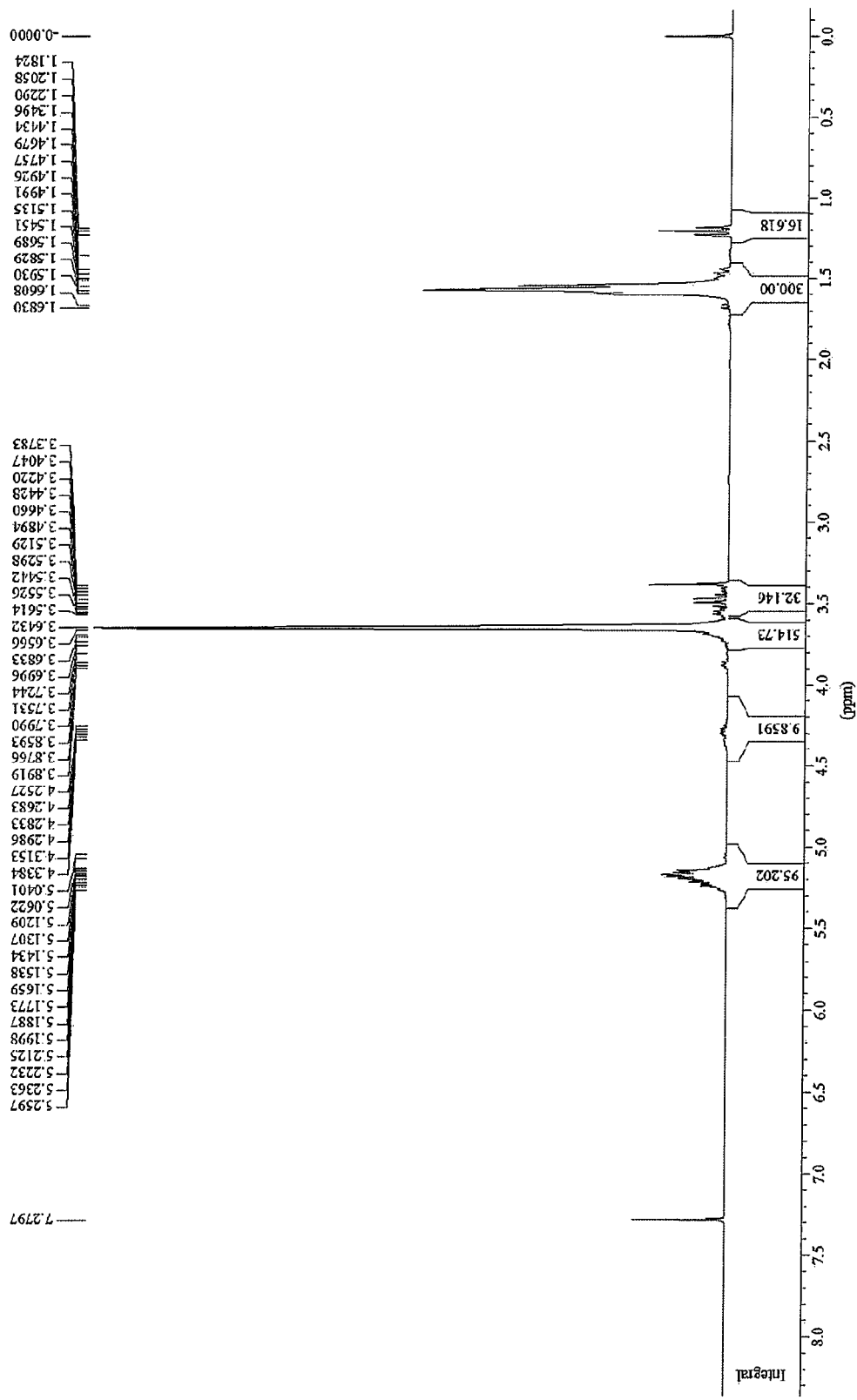
FIG. 5 shows a $^1$H-NMR spectrum of mPEG-PDLLA products prepared by vacuum method ($^1$H-NMR CDCl$_3$ 303K AV-300).
Figure 6:
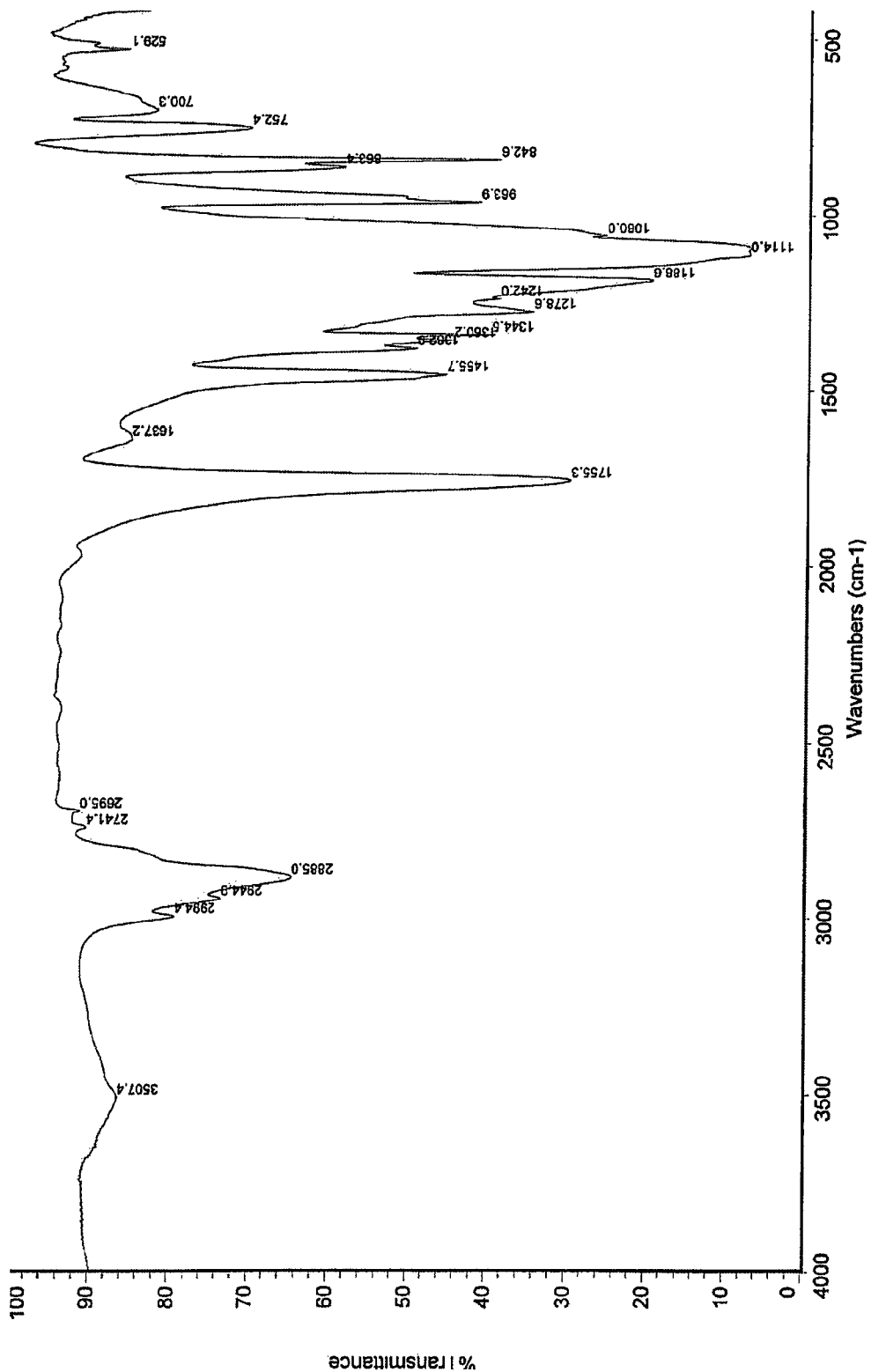
FIG. 6 shows a infrared absorption spectrum (Nexus 870 FT-IR) of mPEG-PDLLA products prepared by vacuum method of the invention.

The embodiments of the present invention are further described by the following examples. To a person skilled in the art, the following examples shouldn't be understood the restriction to the scope of the invention claims.

PREPARATIVE EXAMPLE

Preparation of monomethoxy poly(ethylene glycol)-poly(D,L-lactic acid) block copolymers (different molecular weights)

Method 1: Preparation of mPEG-PDLLA by solvent method

Reaction scheme:

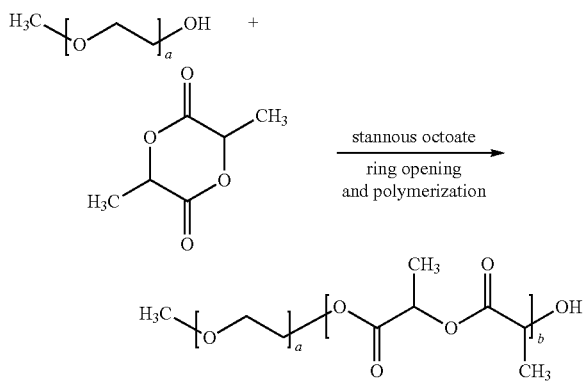

Feed

| Name | Molecular weight | Amount | Remark | Source |
|---|---|---|---|---|
| Monomethoxy poly (ethylene glycol) | 2000 | 8 g | anhydrous | Acros |
| lactide | 144.13 | 12 g | anhydrous | Acros |
| Toluene | / | 80 ml | anhydrous | Nanjing Chemical Reagent Co. |
| Stannous octoate | 405.1 | 0.24 ml | anhydrous | Acros |
| Dichloromethane | / | 3 * 8 ml | / | Nanjing Chemical Reagent Co. |
| Ether | / | 3 * 200 ml | / | Nanjing Chemical Reagent Co. |

Processing:
1. To a reaction flask were added dry monomethoxy poly (ethylene glycol) (MPEG) 8 g, lactide (PLA) 12 g, toluene 80 ml, stannous octoate 0.24 ml, under the nitrogen environment;
2. with stirring, the reaction system was heated to reflux, and held for 16 hours.
3. the reaction solution was cooled to 60° C., and concentrated to dryness at 60° C. under reduced pressure.
4. 8 ml of dichloromethane was added, and stirred to dissolve, then 200 ml of cold ether was added and stirred to grow crystal for 1 hour.

5. suction filtered, and the filter cake was rinsed by cold ether.
6. repeat 4~5 operation to refine twice.
7. the product was dried at 20° C. under vacuum to offer 15 g of white solid, yield: 75%.

Note: (1) molecular weight was detected by a nuclear magnetic instrument: 4878 (cal. 5000).
(2) ratio of PLA/mPEG by weight: 59/41=1.44 (cal. 1.5).
(3) DSC, $^1$H-NMR and IR spectrum of the product referred to Drawing 1, 2 and 3, respectively.

Method 2: Preparation of mPEG-PDLLA by vacuum solid-phase synthesis method

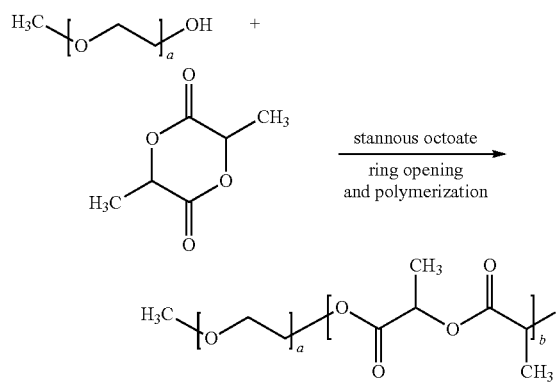

Feed

| Name | Molecular weight | Amount | Remarks | source |
|---|---|---|---|---|
| Monomethoxy poly (ethylene glycol) | 2000 | 8 g | Anhydrous | Acros |
| Lactide | 144.13 | 12 g | Anhydrous | Acros |
| Toluene | / | 80 ml | Anhydrous | Nanjing Chemical Reagent Co. |
| Stannous octoate | 405.1 | 0.24 ml | Anhydrous | Acros |
| Dichloromethane | / | 3 * 8 ml | 3 * 1 | Nanjing Chemical Reagent Co. |
| Ether | / | 3 * 200 ml | 3 * 25 | Nanjing Chemical Reagent Co. |

Processing:
1. To a single-neck flask was added 8 g of monomethoxy poly(ethylene glycol) (MPEG), nitrogen gas was used to purge three times, and vacuated, heated to 120° C., melted and dehydrated for 2 hours. Cooled to 120° C. for later use.
2. To another one-neck flask was added lactide (PLA), vacuated and heated up to 80° C., then dehydrated for 2 hours.
3. Nitrogen was introduced into the flask which was in the vacuum, weighed 12 g of lactide and added into MPEG, then added 0.24 ml of solution of stannous octoate;
4. vacuated, and heated up to 150° C., then reacted for 10 hours, release the vacuum, subsequently the reaction solution was cooled to 20° C.
5. 8 ml of dichloromethane was added, and stirred to dissolve, then 200 ml of cold ether was added and stirred to grow crystal for 1 hour.
6. suction filtered, and the filter cake was rinsed by cold ether.
7. repeated 5~6 operation to refine the wet product twice.
8. the filter cake was dried at 20° C. under vacuum to offer 15 g of white solid, yield: 75%.

Note: (1) molecular weight was detected by a nuclear magnetic instrument: 4651 (cal. 5000).
(2) ratio of PLA/MPEG by weight: 57/43=1.33 (cal. 1.5).
(3) $^1$H-NMR, DSC and IR spectrum of the product referred to Drawing 1, 2 and 3, respectively.

According to the above preparing methods and processes, the feeding ratio of MPEG to lactide was modified to prepare different molecular weight of mPEG-PDLLA, and results were as following:

I. Solvent Method:

| MPEG feeding amount | PLA feeding amount | MW | Calculated MW | Ratio of PLA/MPEG by weight | Calculated ratio of PLA/MPEG by weight |
|---|---|---|---|---|---|
| 8 g | 22 g | 7280 | 7500 | 2.64 | 2.75 |
| 8 g | 16 g | 5840 | 6000 | 1.92 | 2 |
| 8 g | 12 g | 4878 | 5000 | 1.44 | 1.5 |
| 8 g | 10 g | 4304 | 4400 | 1.15 | 1.2 |
| 8 g | 8 g | 3920 | 4000 | 0.96 | 1 |
| 8 g | 6 g | 3440 | 3500 | 0.72 | 0.75 |

II. Vacuum Solid-Phase Synthesis Method:

| MPEG feeding amount | PLA feeding amount | MW | Calculated MW | Ratio of PLA/MPEG by weight | Calculated ratio of PLA/MPEG by weight |
|---|---|---|---|---|---|
| 8 g | 24 g | 7340 | 8000 | 2.67 | 3 |
| 8 g | 22 g | 6880 | 7500 | 2.44 | 2.75 |
| 8 g | 16 g | 5560 | 6000 | 1.78 | 2 |
| 8 g | 12 g | 4680 | 5000 | 1.34 | 1.5 |
| 8 g | 10 g | 4140 | 4400 | 1.07 | 1.2 |
| 8 g | 8 g | 3780 | 4000 | 0.89 | 1 |
| 8 g | 6 g | 3340 | 3500 | 0.67 | 0.75 |

Note: the yields were calculated in 75%; The weight obtained: (MPEG feeding amount + PLA feeding amount) * 0.75

Example 1

Method 1

| Voriconazole formulation for intravenous administration | | | |
|---|---|---|---|
| Constituents | Specification | Amount | Source |
| voriconazole | ≥99% | 1.00 g | Cavendish Co. |
| Excipient mPEG-PDLLA | 3500~4500 | 20.0 g | Cavendish Co. |
| Water for injection | Chinese Pharmacopoeia | Up to 100 ml | |
| Total | | 100 ml | |

To the monomethoxy poly(ethylene glycol)-poly(D,L-lactic acid) block copolymers (mPEG-PDLLA) was added water for injection, and stirred till dissolved; under the successively stirring, voriconazole was added and stirred till dissolved. Activated charcoal was added after voriconazole was dissolved, and sufficiently stirred for 30 mins; then filtered through 0.45 μm filter film to remove the activated charcoal; The filtrate was filtered again through 0.22 μm filter film, then a certain volume of solution was filled in a vial, and lyophilized to offer the lyophilized formulation.

Method 2

| Voriconazole formulation for intravenous injection | | | |
|---|---|---|---|
| Constituents | Specification | Amount | Source |
| Voriconazole | ≥99% | 1.00 g | Cavendish Co. |
| Excipient mPEG-PDLLA | 4500~5500 | 15.0 g | Cavendish Co. |
| Acetonitrile | Chromatographic pure | 10 ml | Merck |
| Water for injection | Chinese Pharmacopoeia | Up to 100 ml | |
| Total | | 100 ml | |

Preparing Process:

To the monomethoxy poly(ethylene glycol)-poly(D,L-lactic acid) block copolymers (mPEG-PDLLA) was added acetonitrile, and stirred till dissolved; with the successively stirring, a solution of voriconazole in acetonitrile was added; after the two solutions were mixed, sufficiently stirred for 30 minutes, then the mixture was concentrated to dryness under reduced pressure. To the resulting viscous liquid was added water for injection with stirring, when the solution became homogenous, activated charcoal was added, and sufficiently stirred for 30 mins; filtered through 0.45 μm filter film to remove the activated charcoal. The filtrate was filtered again through 0.22 μm filter film, then a certain volume of solution was filled in a vial, and lyophilized to offer the lyophilized formulation.

Method 3

| Voriconazole formulation for intravenous injection | | | |
|---|---|---|---|
| Constituents | Specification | Amount | Source |
| Voriconazole | ≥99% | 1.00 g | Cavendish Co. |
| Excipient mPEG-PDLLA | 5500~6500 | 25.0 g | Cavendish Co. |
| Ethanol | Chromatographic pure | 30 ml | |
| Water for injection | Chinese Pharmacopoeia | Up to 100 ml | |
| Total | | 100 ml | |

Preparing Process:

To the monomethoxy poly(ethylene glycol)-poly(D,L-lactic acid) block copolymers (mPEG-PDLLA) was added ethanol, and stirred till dissolved; with the successively stirring, a solution of voriconazole in ethanol was added; after the two solutions were mixed, sufficiently stirred for 30 minutes, then the mixture was concentrated to dryness under reduced pressure. To the resulting viscous liquid was added water for injection with stirring, when the solution became homogenous, activated charcoal was added, and sufficiently stirred for 30 mins; filtered through 0.45 μm filter film to remove the activated charcoal. The filtrate was filtered again through 0.22 μm filter film, then a certain volume of solution was filled in a vial, and lyophilized to offer the lyophilized formulation.

Method 4

| Voriconazole formulation for intravenous administration: | | | |
|---|---|---|---|
| Constituents | Specification | Amount | Source |
| Voriconazole | ≥99% | 1.00 g | Cavendish Co. |
| Excipient mPEG-PDLLA | 6500~7500 | 30.0 g | Cavendish Co. |
| Acetone | Chromatographic pure | 25 ml | |
| Water for injection | Chinese Pharmacopoeia | Up to 100 ml | |
| Total | | 100 ml | |

Preparing Process:

To the monomethoxy poly(ethylene glycol)-poly(D,L-lactic acid) block copolymers (mPEG-PDLLA) was added acetone, and stirred till dissolved. Under the successively stirring, voriconazole powder was added, and stirred till dissolved, sufficiently stirred for 30 minutes, then the mixture was concentrated to dryness under reduced pressure. To the resulting viscous liquid was added water for injection with stirring, when the solution became homogenous, activated charcoal was added, and sufficiently stirred for 30 mins; filtered is through 0.45 μm filter film to remove the activated charcoal; The filtrate was filtered again through 0.22 μm filter film, then a certain volume of solution was filled in a vial, and lyophilized to offer the lyophilized formulation.

The lyophilized formulation prepared by the Method 1 in Example 1 was diluted with water for injection, and stood for 1, 2, 3, 4, 6, 8, 12, 18, and 24 hours at 10° C., 20° C., and 30° C., respectively, then the related substances and enantiomer (2S,3R) and the variation of contents thereof were determined, and the results were detailed in table 1, table 2 and table 3.

The lyophilized formulation prepared by the Method 1 in Example 1 was determined under the condition that the temperature was 40° C., relative humidity was 75% for 1, 2, 3, 6 months according to the method of Accelerated Testing in Chinese Pharmacopoeia, and the related substances and enantiomer (2S,3R) and the variation of contents thereof were determined, and the results were detailed in table 4.

The assay methods of the related substances, enantiomer (2S,3R) and content of voriconazole in the above lyophilized formulations are as following:

1. The Related Substances

Assay method: high-performance liquid phase chromatography

Instrument: high-performance liquid phase chromatographic instrument

Assay Conditions and Method:

Octadecylsilyl bonded silica gel as bulking agent, acetonitrile-1% triethylamine aqueous solution (pH is adjusted to 6.0 by phosphoric acid) (50:50) as mobile phase, detection wavelength at 256 nm.

Test solution (a): dissolve an appropriate amount of the above formulation powder (about equivalent to 50 mg of voriconazole) in the mobile phase in 100 ml volumetric flask, and dilute to 100 ml with the mobile phase.

Reference solution (a): accurately measure 1 ml of test solution (a) in 100 ml volumetric flask and dilute to 100 ml with the mobile phase.

The assay is performed under chromatography condition of assay. Inject 20 μl of reference solution (a). Adjust the sensitivity of the system so that the height of the peak corresponding to the major constituent in the chromatogram obtained is 10~25% of the full scale of the recorder. Inject again 20 μl of test solution (a). Record the chromatogram.

Method of Calculation:

If there are peaks of impurities in the chromatogram obtained with test solution (a), measure the sum of the area of each impurities peaks. which should not be greater than 1.0 percent of the area of the major constituent peak in reference solution (a) (1.0%).

2. Enantiomer (2S,3R):

Assay method: high-performance liquid chromatography

Instrument: high-performance liquid chromatographic instrument

Assay Conditions and Method:

Chiral colume (CHIRALCEL OD-RH 150×4.6 mm), acetonitrile-water (30:70) as mobile phase, detection wavelength at 256 nm. The resolution of two isomer's peaks in the test solutions for system suitability should be meet the specification.

Accurately weight 25 mg of voriconazole reference in 50 ml volumetric flask and dilute with the mobile phase to 50 ml. Then accurately measure 10 ml of voriconazole reference solution and 1 ml of isomer reference stock solution in 50 ml volumetric flask, dilute to 50 ml with the mobile phase. Each 1 ml of this resulting solution comprises 100 μg of voriconazole and 10 μg of its isomer, use as test solution for system suitability.

Isomer stock solution: Accurately weight 25 mg of voriconazole isomer reference in 50 ml volumetric flask, dilute with the mobile phase to 50 ml.

Reference solution (b) of voriconazole isomer: Accurately measure 1 ml of the above solution in 200 ml volumetric flask and dilute to 200 ml with the mobile phase.

Test solution (b): Weight accurately about 50 mg of the product in 100 ml volumetric flask, dilute with the mobile phase to 100 ml.

Inject 20 μl of isomer reference solution (b) and 20 μl of test solution (b) respectively, and record the chromatogram.

Method of Calculation

If there is a peak in the chromatogram of the test solution (b) which retention time is the same as the peak in the chromatogram of the reference solution (b), Calculate the content of the isomer by external standard method, 3. Content Assay method: high-performance liquid chromatography Instrument: high-performance liquid chromatographic instrument Assay Conditions and Method:

Octadecylsilyl bonded silica gel as bulking agent, acetonitrile-1% triethylamine aqueous solution (pH is adjusted to 6.0 by phosphoric acid) (50:50) as mobile phase, detection wavelength at 256 nm.

Test solution (c): Accurately weight an appropriate amount of the above formulation powder (equivalent to about 50 mg of voriconazole) in 100 ml volumetric flask, dilute with mobile phase to 100 ml. Accurately measure 10 ml in 50 ml volumetric flask, dilute with the mobile phase to 50 ml Inject 20 μl of test solution (c), and record the chromatogram.

Then, accurately weight another appropriate amount of voriconazole reference, and determine by the same method.

Method of Calculation:

Calculate the content of voriconazole from the area of peak by external standard method.

The lyophilized formulation prepared by the Method 1 in Example 1 was tested according to the method of long term Testing in Chinese Pharmacopoeia, and the related substances and enantiomer (2S,3R) and the variation of contents thereof were measured under the condition that the temperature was 40° C., relative humidity was 75%, for 1, 2, 3, 6 months (the assay method was the same as above), and the results were detailed in table 5.

TABLE 1 lyophilized formulation (the related substances) (marketed formulation attached as a control)

| time | sample of Example (%) | | | marketed lyophilized powder (%) | | | marketed sterile powder (%) | | |
| --- | --- | --- | --- | --- | --- | --- | --- | --- | --- |
| (hour) | 10° C. | 20° C. | 30° C. | 10° C. | 20° C. | 30° C. | 10° C. | 20° C. | 30° C. |
| 1 | 0.08 | 0.08 | 0.09 | 0.09 | 0.08 | 0.09 | 0.09 | 0.08 | 0.09 |
| 2 | 0.08 | 0.09 | 0.08 | 0.09 | 0.09 | 0.09 | 0.08 | 0.09 | 0.09 |
| 3 | 0.09 | 0.09 | 0.09 | 0.10 | 0.09 | 0.10 | 0.09 | 0.09 | 0.10 |
| 4 | 0.08 | 0.08 | 0.08 | 0.10 | 0.10 | 0.09 | 0.10 | 0.09 | 0.11 |
| 6 | 0.09 | 0.09 | 0.10 | 0.09 | 0.09 | 0.10 | 0.10 | 0.09 | 0.10 |
| 8 | 0.10 | 0.09 | 0.09 | 0.10 | 0.09 | 0.10 | 0.09 | 0.10 | 0.10 |
| 12 | 0.09 | 0.10 | 0.11 | 0.11 | 0.10 | 0.11 | 0.10 | 0.10 | 0.11 |
| 18 | 0.09 | 0.10 | 0.10 | 0.11 | 0.11 | 0.12 | 0.10 | 0.11 | 0.12 |
| 24 | 0.10 | 0.10 | 0.12 | 0.11 | 0.12 | 0.12 | 0.12 | 0.11 | 0.12 |

TABLE 2 lyophilized formulation (enantiomer) (marketed formulation attached as a control)

| | enantiomer | | | | | | | | |
|---|---|---|---|---|---|---|---|---|---|
| | sample of example (%) | | | lyophilized powder marketed (%) | | | sterile powder marketed (%) | | |
| time (hour) | 10° C. | 20° C. | 30° C. | 10° C. | 20° C. | 30° C. | 10° C. | 20° C. | 30° C. |
| 1 | ND | ND | ND | ND | ND | ND | ND | ND | ND |
| 2 | ND | ND | ND | ND | ND | ND | ND | ND | ND |
| 3 | ND | ND | ND | ND | ND | ND | ND | ND | ND |
| 4 | ND | ND | ND | ND | ND | ND | ND | ND | ND |
| 6 | ND | ND | ND | ND | ND | ND | ND | ND | ND |
| 8 | ND | ND | ND | ND | ND | 0.01 | ND | ND | 0.01 |
| 12 | ND | ND | ND | ND | 0.01 | 0.01 | 0.01 | 0.01 | 0.02 |
| 18 | ND | ND | ND | ND | 0.02 | 0.02 | 0.01 | 0.02 | 0.02 |
| 24 | ND | ND | ND | 0.01 | 0.02 | 0.03 | 0.02 | 0.02 | 0.03 |

ND = not detected

TABLE 3 lyophilized formulation (contents) (marketed formulation attached as a control)

| | content | | | | | | | | |
|---|---|---|---|---|---|---|---|---|---|
| | sample of example (%) | | | lyophilized powder marketed (%) | | | sterile powder marketed (%) | | |
| time (hour) | 10° C. | 20° C. | 30° C. | 10° C. | 20° C. | 30° C. | 10° C. | 20° C. | 30° C. |
| 1 | 99.79 | 99.80 | 99.79 | 99.76 | 99.85 | 99.76 | 99.75 | 99.76 | 99.75 |
| 2 | 99.80 | 99.76 | 99.78 | 99.78 | 99.83 | 99.75 | 99.74 | 99.75 | 99.73 |
| 3 | 99.77 | 99.78 | 99.76 | 99.74 | 99.86 | 99.76 | 99.75 | 99.73 | 99.71 |
| 4 | 99.78 | 99.77 | 99.79 | 99.74 | 99.83 | 99.74 | 99.73 | 99.74 | 99.70 |
| 6 | 99.78 | 99.81 | 99.74 | 99.75 | 99.85 | 99.73 | 99.70 | 99.71 | 99.71 |
| 8 | 99.76 | 99.77 | 99.78 | 99.75 | 99.84 | 99.74 | 99.71 | 99.68 | 99.68 |
| 12 | 99.80 | 99.75 | 99.75 | 99.76 | 99.82 | 99.75 | 99.68 | 99.66 | 99.66 |
| 18 | 99.77 | 99.74 | 99.73 | 99.74 | 99.83 | 99.71 | 99.67 | 99.67 | 99.65 |
| 24 | 99.75 | 99.76 | 99.73 | 99.76 | 99.82 | 99.72 | 99.68 | 99.66 | 99.65 |

TABLE 4

Results of experiments for the accelerated testing of lyophilized formulation (marketed formulation attached as a control)

| | sample of example (%) | | | lyophilized powder marketed (%) | | | sterile powder marketed (%) | | |
|---|---|---|---|---|---|---|---|---|---|
| time (month) | the related substances | enantiomer | content | the related substances | enantiomer | content | the related substances | enantiomer | content |
| 0 | 0.09 | ND | 99.81 | 0.08 | ND | 99.83 | 0.09 | ND | 99.80 |
| 1 | 0.13 | ND | 99.79 | 0.12 | ND | 99.80 | 0.13 | ND | 99.77 |
| 2 | 0.15 | ND | 99.74 | 0.14 | ND | 99.75 | 0.15 | ND | 99.74 |
| 3 | 0.19 | ND | 99.69 | 0.18 | 0.01 | 99.71 | 0.18 | ND | 99.68 |
| 6 | 0.19 | ND | 99.68 | 0.20 | 0.02 | 99.65 | 0.20 | 0.01 | 99.64 |

TABLE 5

Results of experiments for long term testing of lyophilized
formulation (marketed formulation attached as a control)

| time (month) | sample of example (%) | | | lyophilized powder marketed (%) | | | sterile powder marketed (%) | | |
| --- | --- | --- | --- | --- | --- | --- | --- | --- | --- |
| | the related substances | enantiomer | content | the related substances | enantiomer | content | the related substances | enantiomer | content |
| 0 | 0.09 | ND | 99.81 | 0.08 | ND | 99.83 | 0.09 | ND | 99.80 |
| 3 | 0.12 | ND | 99.78 | 0.11 | ND | 99.80 | 0.11 | ND | 99.78 |
| 6 | 0.13 | ND | 99.75 | 0.14 | ND | 99.76 | 0.13 | ND | 99.79 |
| 9 | 0.15 | ND | 99.74 | 0.17 | ND | 99.74 | 0.16 | ND | 99.75 |
| 12 | 0.18 | ND | 99.75 | 0.19 | ND | 99.74 | 0.18 | ND | 99.72 |
| 18 | 0.18 | ND | 99.74 | 0.20 | 0.01 | 99.72 | 0.19 | 0.01 | 99.71 |
| 24 | 0.19 | ND | 99.71 | 0.20 | 0.02 | 99.72 | 0.20 | 0.01 | 99.68 |

The lyophilized formulation (prepared by the Method 1 in Example 1 as above) was dissolved by water for injection to prepare as an aqueous solution, then diluted by 0.9% sodium chloride injection to prepare as infusion for clinically use. The data for solubility of sample of Example and the solubility of marketed formulation measured by the same method were shown in Table 6.

TABLE 6

Results of experiments for solubility of lyophilized formulation
(marketed formulation attached as a control)

| | sample of example (%) | | lyophilized powder marketed (%) | | sterile powder marketed (%) | |
| --- | --- | --- | --- | --- | --- | --- |
| | WFI | 0.9% NaCl injection | WFI | 0.9% NaCl injection | special solvent | 0.9% NaCl injection |
| dissolving rate | 60 seconds | 15 seconds | 60 seconds | 15 seconds | 120 to 180 seconds | 180 seconds |
| concentration appearance | 10 mg/ml clear | 5 mg/ml clear | 10 mg/ml clear | 5 mg/ml clear | 20 mg/ml clear | 0.8 mg/ml cystal precipited |

WFI: water for injection

Comparison of safety for excipient monomethoxy poly(ethylene glycol)-poly(D,L-lactic acid) (mPEG-PDLLA) of formula (I), with sulfobutyl ether β-cyclodextrin sodium (SB-ECD), and special organic solvents (propylene glycol-ethanol 2:3) were shown in table 7.

TABLE 7 comparison of safety

| | mPEG-PDLLA | SBECD | propylene glycol-ethanol (2:3) |
| --- | --- | --- | --- |
| hemolyticus | i.v. 6 mg/ml could cause hemolysis. | mild hemolysis occurs i.v. at 0.02 mg/ml, and significant heamolysis at 0.04 mg/ml. | propylene glycol: continuously administrated at 7700 mg/infusing 4 hours/day for 5 days, no hemolysis and no effects to the red blood cell. |
| reproductive toxicity mutagenes-is carcinogenesity | no references showed positive characteristic in the "three genicities". The excipient is safe. | In the two-year animal teratogenicity and carcinogenecity studies, some evidences demonstrated that it was carcinogenic (pancreatic carcinoma) in rodent. | propylene glycol: reproductive toxic studies showed that no abnormity had been observed in the long term fertility study, and, NOAEL of maternal toxicity in teratogenic sensitive period and teratogenic toxicity in rats and mice are all 1600 mg/kg/day. Ethanol could cause damage of spermatogenic cells, inhibit the synthesis of steroids, and damage the reproductive endocrine function of hypothalamic-pituitary axis |

TABLE 7-continued

| | comparison of safety | | |
|---|---|---|---|
| | mPEG-PDLLA | SBECD | propylene glycol-ethanol (2:3) |
| acute toxicity | No occurrence of death, and phenomena of intoxication or delayed intoxication had been observed in mice i.v. at 2000 mg/kg; | i.v., in mice and rat, LD50 > 2000 mg/kg | propylene glycol, in rat, i.v. LD50 ≥ 5000 mg/kg. ethanol, in rat, i.v. LD50 = 1973 mg/kg; in mice, i.v. LD50 = 1440 mg/kg. |
| long-term toxicity | After continuously administered i.v. for three months at 1000 mg/kg, and 5% glucose solution as a control group, in contrast to the control group, the differences of body weight, food consumption, and blood testing in the mPEG-PDLLA group had not been observed, the tissue structural abnormity relative to drug toxicity had not been observed in the sample testing and pathologic testing; the observations for restoration of rats in treatment group had shown that delayed toxicity had not occurred | The mild heptotoxity may be observed at 10~30 mg/kg/day in mice, and at 10~30 mg/kg/day in rats continuously administrated for two years. The weight of mice were significantly decreased after administration at 18 mg/kg/day or higher dose. | |

The invention claimed is:

1. A pharmaceutical formulation comprising voriconazole and an excipient "monomethoxy poly (ethylene glycol)-poly (D,L-lactic acid) block copolymers (mPEG-PDLLA)" of formula (I) as follows:

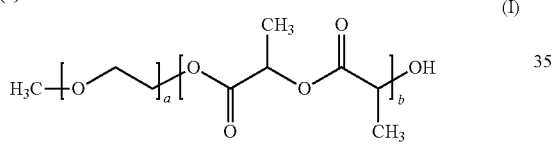

molecular formula: $CH_3(C_2H_4O)_a(C_6H_8O_4)_bOH$ wherein, a in the copolymer is 35-50, b is 12-36, and the average molecular weight is in the range of 3300-7500, the content of voriconazole is about 4.8% by weight; and the weight ratio of voriconazole to copolymers of formula (I) is 1:20.

* * * * *